United States Patent [19]

Eichman

[11] 4,253,477
[45] Mar. 3, 1981

[54] DENTAL FLOSS HOLDER

[76] Inventor: John J. Eichman, 212 Haddon Ave., Westmont, N.J. 08108

[21] Appl. No.: 63,079

[22] Filed: Aug. 2, 1979

[51] Int. Cl.³ .............................................. A61C 15/00
[52] U.S. Cl. ..................................................... 132/91
[58] Field of Search ..................................... 132/91–92

[56] References Cited

U.S. PATENT DOCUMENTS

| | | | |
|---|---|---|---|
| 3,311,116 | 3/1967 | Foster | 132/92 R |
| 3,378,017 | 4/1968 | Stiles | 132/92 R |
| 3,886,956 | 6/1975 | Cash | 132/91 |

Primary Examiner—G. E. McNeill
Attorney, Agent, or Firm—Robert K. Youtie

[57] ABSTRACT

Described herein is a dental floss holder including a head for entry into a person's mouth and carrying an extended length of dental floss for entry between the user's teeth, the head being provided opposite to the dental floss with a bite member for engagement by the user's teeth to forcibly effect dental floss entry, and a lever having one end swingable into engagement with the user's teeth to withdraw dental floss from between the teeth.

7 Claims, 5 Drawing Figures

DENTAL FLOSS HOLDER

BACKGROUND OF THE INVENTION

While there have, in the past, been proposed a large variety of dental floss holders to facilitate engagement of dental floss between a user's teeth, such devices have not been entirely satisfactory, being difficult to set up or prepare for use with fresh floss, requiring undue dexterity and strength for inserting floss between the teeth, being relatively complex and expensive to manufacture, and otherwise not acceptable to the mass market.

As examples of prior patents disclosing dental floss holders, there are the following:

| U.S. Pat. No. | Inventor |
| --- | --- |
| 1,415,765 | Bailey |
| 1,910,740 | Barsha |
| 2,384,712 | Turenchalk et al |
| 2,650,598 | Rodesci |
| 2,873,749 | Gjerde |
| 3,236,247 | Brockman |

SUMMARY OF THE INVENTION

It is, therefore, an important object of the present invention to provide a dental floss holder which is extremely simple in construction for economy in cost and durablity throughout a long useful life, which is capable of quick and easy operation to greatly speed and facilitate the flossing procedure, and which affords unique and advantageous modes of floss insertion and withdrawal with respect to the user's teeth, all with only a modicum of effort and dexterity, and further which greatly simplifies, sanitizes and enhances the appearance of the flossing operation, to make the same more presentable in polite company.

Other objects of the present invention will become apparent upon reading the following specification and referring to the accompanying drawings, which form a material part of this disclosure.

The invention accordingly consists in the features of construction, combinations of elements, and arrangements of parts, which will be exemplified in the construction hereinafter described, and of which the scope will be indicated by the appended claims.

DESCRIPTION OF THE PREFERRED EMBODIMENT

Figure 1:
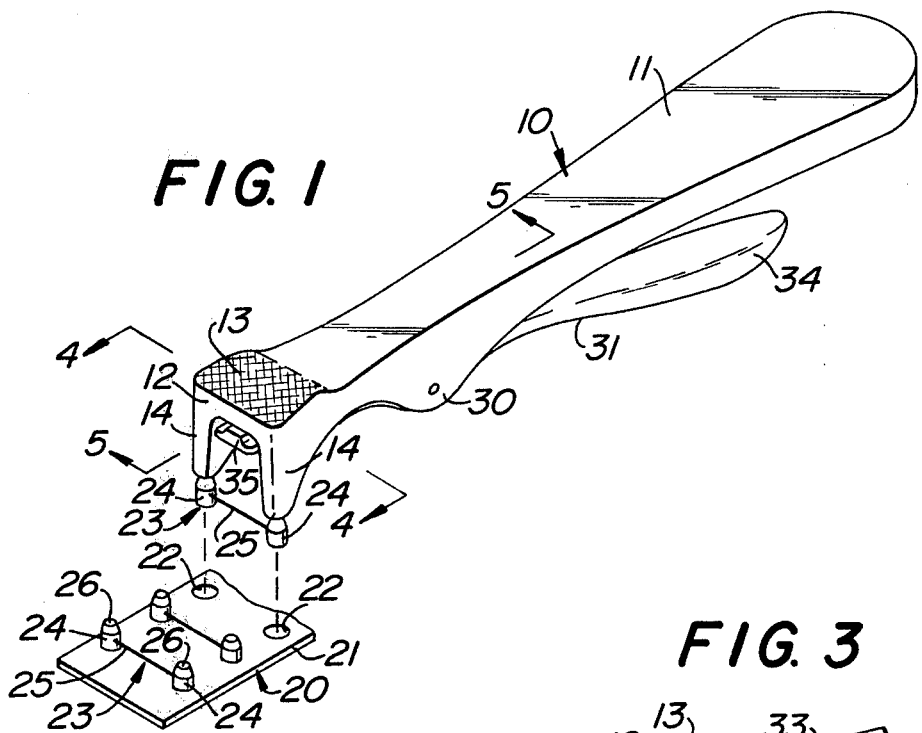
FIG. 1 is a perspective view showing a dental floss holder of the present invention in operative association with a supply of dental floss for use with the holder.

Referring now more particularly to the drawings, and specifically to FIG. 1 thereof, a dental floss holder of the present invention is there generally designated 10, and may include a elongate manual gripping member or handle 11. Extending from one end of the handle 11, longitudinally thereof, is an enlarged member or head 12, say of generally rectangular configuration. Provided on one side of the head 12, say the upper side as seen in the drawings, is a frictional boss or pad, or bite member 13, for engagement by a user's teeth, as will appear more fully hereinafter.

Figure 4:
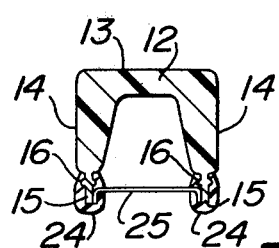
FIG. 4 is a transverse sectional view taken generally along the line 4—4 of FIG. 1.

Extending from the other lower side of head 12, as seen in the drawings, spaced laterally of the head apart from each other, are a pair of depending protrusions or legs 14. Projecting from the distal end of each leg 14, is a pin 15, see FIG. 4, which cooperates to provide floss holding means, as will appear presently. The distal end members or pins 15 may be provided with generally annular, circumferential enlargements or beads, as at 16.

Referring again to FIG. 1, there is shown therein a floss package or dispenser 20, including a carrier or sheet 21 provided with spaced pairs of receivers or holes 22. Removably carried in each pair of laterally spaced holes 22 may be a floss assembly 23, including a pair of anchors, tubes or caps 24 respectively located in the associated holes 22, and a length of floss 25 extending between and having its opposite ends suitably affixed to respective anchors 24. Each of the anchors or caps 24 is provided with a central, upwardly opening hole, as at 26 adapted to receive a respective leg extension or pin 15.

More specifically, by easy manipulation, a pair of leg extensions or pins 15 are engaged downwardly into respective caps or anchors 24, into snap interengagement therewithin; and, the floss holder or tool 10 may then be withdrawn upwardly to the position shown in FIG. 1 with the caps 24 and floss 25 anchored to the legs 14.

Spaced inwardly from the head 12, on the inner or under side thereof as seen in the drawings, the handle 11 is provided with a pair of laterally spaced part depending lugs or ears 30. A lever 31 extends longitudinally and along the under side of handle 11, and includes a lever portion 32 passing between lugs 30. A pivotal mounting, axle or pin 33 extends between laterally opposed lugs 30 and through intermediate lever portion 32, to thereby mount the lever 31 for swinging movement about the laterally extending or transverse axis of pin 33. By the lever configuration, best seen in FIG. 5, the lever is mounted for a substantial degree of swinging movement of its finger gripping portion 34 toward and away from the handle 11.

Figure 3:
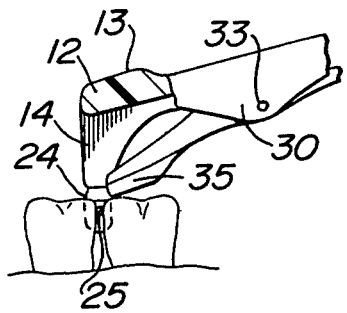
FIG. 3 is a partial side elevational view similar to FIG. 2, but illustrating a floss withdrawal operation employing the instant apparatus.
Figure 5:
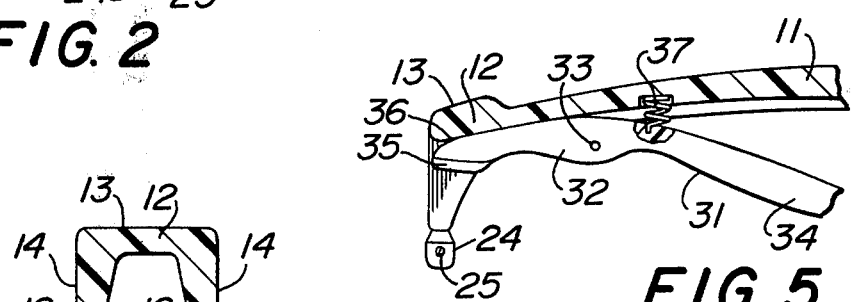
FIG. 5 is a partial longitudinal sectional view taken generally along the line 5—5 of FIG. 1.

Extending from the lever 31, beyond the pivot pin 33 and lever portion 32, is a bearing member 35 which is generally located between the legs 14 and swingable about the pin axis 33 generally longitudinally of the legs. In a limiting position of the lever 31, the upper or outer surface 36 of bearing member 35 may be in limiting engagement with the under or inner side of head 12. Upon swinging movement of the lever 31, the bearing member 35 moves generally transversely of the handle 11, away from the head 12, generally longitudinally of the legs 14 toward the leg extensions or pins 15. However, the distal end of bearing member 35 terminates short of the floss 25 upon such swinging movement of the bearing member away from the head, as seen in FIG. 3. Suitable resilient means, such as a coil spring 37, may be interposed between the handle 11 and lever 31, to urge the latter clockwise, as seen in FIG. 5. Thus, the bearing member 35 is urged toward its retracted position adjacent to the head 12.

Figure 2:
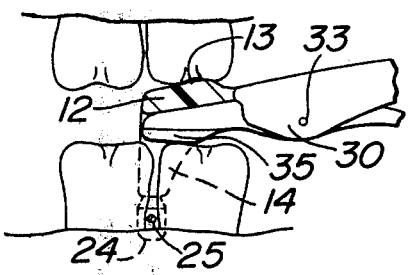
FIG. 2 is a partial side elevational view, partly in section, illustrating the procedure for inserting floss between a pair of adjacent teeth.

In operation, with a floss assembly 23 in position on the legs 14, the handle 11 is manipulated to place the head 12 in a user's mouth and the legs on opposite sides of a row of teeth, say the lower row of teeth. Very conveniently, a tooth of the upper row may engage in biting relation with the bite member 13 to facilitate forcible engagement of floss between an adjacent pair of the user's lower teeth, if forcible entry is necessary. This operation, and the resultant condition are shown in FIG 2. The floss manipulation may then be manually achieved to effect dislodgement of foreign material between the teeth.

Subsequent removal of the floss 25 from the teeth may be quickly and easily effected by mere manual gripping and squeezing of the handle 11 and lever 31 to swing the bearing member 35 against a tooth and thereby shift the head 12 away from the teeth and withdraw the floss 25 from between the teeth. This operation is shown in FIG. 3. Of course, a desired degree of force multiplication may be achieved by appropriate design of lever 31.

If the floss 25 remains in satisfactory condition after withdrawal from between the user's teeth, it may be reused by repeating the above described procedure. Otherwise, the floss may be removed by removal of the anchors or caps 24 and the floss assembly discarded and replaced by a fresh floss assembly, in a manner described hereinbefore.

From the foregoing, it is seen that the present invention provides a holder for dental floss which greatly facilitates the flossing operation, especially for persons whose tooth spacing is minimal and requires forcible floss interposition, which enhances the aesthetic appearance of the flossing operation, being relatively economical, and otherwise accomplishes its intended objects.

Although the present invention has been described in some detail by way of illustration and example for purposes of clarity of understanding, it is understood that certain changes and modifications may be made within the spirit of the invention.

What is claimed is:

1. A holder for dental floss, said holder comprising a handle for manual gripping, a head extending generally longitudinally from said handle for entry into a user's mouth, a pair of spaced legs extending from one side of said head transversely of said handle for respective location on opposite sides of one row of the user's teeth, floss holding means on said legs for holding a length of floss in bridging relation across the space between said legs, a bit member on the other side of said head located to be bitten by a user's teeth of the other row to engage the floss between adjacent teeth of said one row, a lever pivoted to said handle for swinging movement actuated by a user's hand, and a bearing member extending from said lever on one side of said head and swingable with said lever toward and away from said head, said bearing member being engageable with teeth of said one row and movable away from said head to disengage floss from between the teeth of said one row.

2. A holder according to claim 1, said bearing member having its extremity terminating short of a length of floss in said bridging relation, to prevent dislodging of the floss by said bearing member.

3. A holder according to claim 2, said lever being pivoted about an axis generally transverse of said handle and legs for swinging said bearing member generally longitudinally of said legs.

4. A holder according to claim 3, in combination with resilient means urging said bearing member toward said head for ease of floss engagement between teeth.

5. A holder according to claim 4, said bearing member in its rest position abutting said head for limiting engagement with teeth of said one row.

6. A holder for dental floss, said holder comprising a handle for manual gripping, a head extending generally longitudinally from said handle for entry into a user's mouth, a pair of spaced legs extending from one side of said head transversely of said handle for respective location on opposite sides of one row of the user's teeth, floss holding means on said legs for holding a length of floss in bridging relation across the space between said legs for engagement between adjacent teeth of said one row, a lever pivoted to said handle for swinging movement actuated by a user's hand, and a bearing member extending from said lever on said one side of said head and swingable with said lever toward and away from said head, said bearing member being engageable with teeth of said one row and movable away from said head to disengage floss from between the teeth of said one row.

7. A holder according to claim 6, said bearing member having its extremity short of a length of floss in said bridging relation to prevent dislodging of the floss by said bearing member, and said lever being pivoted about an axis generally transverse of said handle and legs for swinging said bearing member generally longitudinally of said legs.

* * * * *